United States Patent [19]

Felix et al.

[11] Patent Number: 5,846,936
[45] Date of Patent: Dec. 8, 1998

[54] GROWTH HORMONE RELEASING FACTOR ANALOGS

[75] Inventors: Arthur Martin Felix, West Caldwell; Edgar Philip Heimer, Nutley, both of N.J.

[73] Assignee: Roche Vitamins Inc., Paramus, N.J.

[21] Appl. No.: 493,594

[22] Filed: Jun. 22, 1995

Related U.S. Application Data

[63] Continuation of Ser. No. 274,656, Jul. 13, 1994, abandoned, which is a continuation of Ser. No. 154,579, Nov. 19, 1993, abandoned, which is a continuation of Ser. No. 993,489, Dec. 18, 1992, abandoned, which is a continuation of Ser. No. 682,835, Apr. 9, 1991, abandoned.

[51] Int. Cl.$^6$ .......................... A61K 38/25; C07K 14/60
[52] U.S. Cl. .................. 514/12; 530/324; 930/DIG. 559
[58] Field of Search ......................... 514/12, 2; 530/324, 530/325, 399; 930/120, 320, DIG. 820, DIG. 822, 824, DIG. 559

[56] References Cited

U.S. PATENT DOCUMENTS

| | | | |
|---|---|---|---|
| 4,517,181 | 5/1985 | Ling et al. | 514/12 |
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,562,175 | 12/1985 | Chang et al. | 514/12 |
| 4,563,352 | 1/1986 | Rivier et al. | 514/12 |
| 4,585,756 | 4/1986 | Brazeau, Jr. et al. | 514/12 |
| 4,595,676 | 6/1986 | Spiess et al. | 514/12 |
| 4,605,643 | 8/1986 | Bohlen et al. | 514/12 |
| 4,610,976 | 9/1986 | Bohlen et al. | 514/12 |
| 4,617,149 | 10/1986 | Di Marchi et al. | 530/324 |
| 4,618,598 | 10/1986 | Conn | 514/6 |
| 4,622,312 | 11/1986 | Felix et al. | 514/12 |
| 4,626,523 | 12/1986 | Vale, Jr. et al. | 514/12 |
| 4,628,043 | 12/1986 | Spiess et al. | 514/12 |
| 4,649,039 | 3/1987 | Garlick et al. | 424/1.1 |
| 4,649,131 | 3/1987 | Felix et al. | 514/12 |
| 4,689,318 | 8/1987 | Kaiser et al. | 514/12 |
| 4,703,035 | 10/1987 | Rivier et al. | 514/12 |
| 4,728,726 | 3/1988 | Rivier et al. | 530/324 |
| 4,732,972 | 3/1988 | Felix et al. | 530/324 |
| 4,734,399 | 3/1988 | Felix et al. | 514/12 |
| 4,783,524 | 11/1988 | Larsen et al. | 530/350 |
| 4,784,987 | 11/1988 | Rivier et al. | 514/12 |
| 4,914,189 | 4/1990 | Schally et al. | 530/324 |

FOREIGN PATENT DOCUMENTS

| | | |
|---|---|---|
| 23075/84 | 1/1984 | Australia . |
| 105759 | 10/1983 | European Pat. Off. . |
| 117034 | 1/1984 | European Pat. Off. . |
| 121764 | 3/1984 | European Pat. Off. . |
| 138416 | 9/1984 | European Pat. Off. . |
| 177819 | 9/1985 | European Pat. Off. . |
| 216517 | 8/1986 | European Pat. Off. . |
| 292334 | 5/1988 | European Pat. Off. . |
| 326 418 | 8/1989 | European Pat. Off. . |
| 0352014 | 1/1990 | European Pat. Off. . |
| 365 779 | 5/1990 | European Pat. Off. . |
| 209 515 | 9/1984 | New Zealand . |
| 8907113 | 8/1989 | WIPO . |
| 90/08776 | 8/1990 | WIPO . |
| 90/8776 | 8/1990 | WIPO . |
| 90/15821 | 12/1990 | WIPO . |

OTHER PUBLICATIONS

Dayhoff, Margaret, Atlas of Protein Sequence and Structure Washington, D.C. National Biomedical Research Foundation, 1973, vol. 5, p. 96.
Schulz, G.E. Principles of Protein Structure. New York: Springer–Verlag, 1979, pp. 14–16.
Tou et al, Biochemical and Biophysical Research Com., vol. 139, No. 2, pp. 763–770, (1986).
Coy et al, J. Med. Chem., vol. 28, pp. 181–185, (1985).
Velicelebi et al, Proc. Nat'l. Acad. Sci. USA, vol. 83, pp. 5397–5399, (Aug. 1986).
Ling et al, "Quao Vadis?", Symposium, Sanofi Group, pp. 309–322 (May, 1985).
Patent Office Journal No. 1311, pp. 672–673 (Jul. 1988).
Felix, A.M. et al., Peptides 1988 Proceeding of the 20th European Peptide Symposium, Tubingen 4–9, pp. 601–603 (1988).
Martinez, J. "Peptide Hormones as Prohormones: Processing, Biological activity, Pharmacology", Ellis Horwood Ltd., Chicester, GB pp. 230–231 (not dated).
Zarandi, M. International Journal of Peptide and Protein Research, vo. 36 (6), pp. 499–505 (1990).
Friedman, et al., International Journal of Peptide and Protein Research, 37 (1) pp. 14–20 (1991).
Chemical Abstracts, vol. 107, Abstract No. 7619, p. 707, col. 1 (1987).
Biochem. Biophys. Res. Comm., 119(1), 265 (1984).
Medical World, Mar. 12, 1984, p. 37.
Proc. 7th Inter. Cong. Endo., Quebec City, Jul. 1–7, 1984, paper N–873.

(List continued on next page.)

Primary Examiner—Jeffrey E. Russel
Attorney, Agent, or Firm—George W. Johnston; Dennis P. Tramaloni; Alan P. Kass

[57] ABSTRACT

Novel growth hormone releasing factor analogs are presented having a sequence of from about twenty-nine (29) to about forty-four (44) amino acids (SEQ ID NO: 6) wherein Xaa at position 1 is His, 3-MeHis, desNH$_2$His, Tyr, or desNH$_2$Tyr; Xaa at position 2 is Val, Leu, lie, Ala, D-Ala, N-Methyl-D-Ala, Gly, NIe, or Nval; Xaa at position 8 is Gln, Ser, or Thr; Xaa at position 15 is Ala or Leu; Xaa at position 27 is Met, Nle or Leu; Xaa at position 28 is Ser or Asn; Xaa at position 29 is an amino acid residue sequence (SEQ ID NO: 7) or fragments thereof where the fragment is reduced in number by one to fifteen amino acid residues from the carboxyl-terminus, where the carboxyl terminus can be the free carboxylic acid or the corresponding amide, and the pharmaceutically acceptable acid or base addition salts thereof. The novel growth hormone releasing factor analogs demonstrate enhanced potency for the release of growth hormone, have enhanced enzymatic stability, improved half-life stability in aqueous solution, and can be administered to a subject having a deficiency of growth hormone or for improvement of growth performance in livestock and other warm blooded animals and in fish and other cold blooded marine animals.

19 Claims, No Drawings

OTHER PUBLICATIONS

Proc. 7th Inter. Cong. Endo., Quebec City, Jul. 1–7, 1984, Abstracts N–885, N–887/889, N–891/893, N–849.
Biochem. Biophys. Res. Comm. 123(2), 497 (1984).
*Biochem. Biophys. Res. Comm.* 123(2), 854 (1984).
*New York Times,* Apr. 17, 1988, p. C1.
*Molecular Endocrinology,* 3(10), 1529 (1989).
*Principals of Biochemistry,* 5th Ed., pp. 1126–1129 (Not Dated).
*Life Sciences,* 46(16), 999 (1990).
Document Abstract of WO 90/15821 (Document AAX) (Dec. 27, 1990).
*Science,* 218(5), 585 (1982).
*Nature,* 300, 276 (1982).
*Proc. Natl. Acad. Sci. USA* 79, 7909 (1982).
*J. Clin. Endo. Metab.* 57(3), 677 (1983).
*Unlisted Drugs,* 35(3), 41 (1983).
*Nature,* 303, 532 (1983).

GROWTH HORMONE RELEASING FACTOR ANALOGS

This is a continuation of application Ser. No. 08/274,656, filed Jul. 13, 1994, now abandoned, which is a continuation of application Ser. No. 08/154,579, filed Nov. 19, 1993, now abandoned, which is a continuation of application Ser. No. 07/993,489, filed Dec. 18, 1992, now abandoned, which is a continuation of application Ser. No. 07/682,835, filed Apr. 9, 1991, now abandoned.

FIELD OF THE INVENTION

This invention relates to analogs of human growth hormone releasing factor and to fragments thereof. The pharmaceutical compositions of the invention can be used to treat a variety of growth hormone related problems in human beings and for performance enhancement in animals.

BACKGROUND OF THE INVENTION

Human growth hormone releasing factor (hGRF or GRF) has been isolated from human islet cell tumor and structurally characterized by Guillemin and co-workers, *Science*, 218, 585–587 (Nov. 5, 1982) and Rivier and co-workers, *Nature*, 300, 276–278 (1982). The isolation and characterization of GRF, while sought for decades, was previously unsuccessful due to its presence in very small quantities. Human hypothalamic growth hormone releasing factor (hGRF) has been shown to have the same structure as GRF isolated from islet cell tumor, by Bohlen et al, *Biochem. and Biophys. Res. Comm.*, 114(3), 930–936 (1983).

Rivier and co-workers, Id., have described the structure of GRF (1–44) (SEQ ID NO: 1) and GRF (1–40) (SEQ ID NO: 2), respectively, and shown that GRF is specific for the release of growth hormone. These two forms of GRF are identical at the amino ($NH_2$) terminal but differ in the termination point of the carboxy (COOH) terminus. GRF (1–44) (SEQ ID NO: 1) is further distinguished in having an amide group at the carboxy terminus.

Rivier and Vale et al, Id., have shown that the biological activity of GRF resides in the $NH_2$-terminal portion of the molecule and full intrinsic activity and potency was demonstrated with GRF(1–29)-$NH_2$ (SEQ ID NO: 3-$NH_2$) in vitro.

Lance et al, *Biochemical and Biophysical Research Communications*, 119(1), 265–272 (1984) have shown that GRF (1–29)-$NH_2$ (SEQ ID NO: 3-$NH_2$) with substitutions of selected amino acids at positions 1, 2 and 3 cause enhanced release of growth hormone (GH) in both pig and rat in vivo.

Friedman et al., *Peptides: Chemistry. Structure and Biology* (*Proceedings of the 11th American Peptide Symposium*), Rivier and Marshall (Eds), Escom, Leiden, p 220 (1990) have recently reported that a slow deamidation of the $Asn^8$ residue in [$Leu^{27}$]-GRF(1–32)-$NH_2$ (SEQ ID NO:4-$NH_2$) (pH 7.4) leads to the formation of [isoAsp$^8$, $Leu^{27}$]-GRF (1–32)-$NH_2$ (SEQ ID NO: 5-$NH_2$ where $Xaa^8$ is isoAsp) and [$Asp^8$, $Leu^{27}$]-GRF(1–32)-$NH_2$ (SEQ ID NO:5-$NH_2$ where $Xaa^8$ is Asp), which have substantially reduced biological activities.

Growth in animals is presumably regulated by a cascade of bioregulatory molecules. The hypothalamus produces GRF which induces pituitary release of growth hormone. Small quantities of GRF have been found to cause substantial pituitary release of growth hormone into the blood. Thus, GRF has great therapeutic utility in those instances where growth hormone is indicated. For example, GRF may be used in the treatment of hypopituitary dwarfism, diabetes due to growth hormone production abnormalities, enhancement of wound healing, treatment of burns, retardation of the aging process or osteoporosis or bone healing. Similarly, GRF has utility in the agricultural field. Examples of agricultural uses include, enhanced meat production of fowl or animals raised for food such as pigs, cattle or the like to permit earlier marketing or to produce larger animals in similar time on feed or improve the lean to fat ratios. GRF may also stimulate milk production in dairy cows and egg production in chickens. In addition, GRF can be used in aquiculture, for example, for raising or accelerating the growth of fish and other cold-blooded marine animals.

The successful isolation of GRF was due partly to the discovery that human pancreatic islet tumors associated with acromegaly ectopically produced large quantities of GRF. Three forms of GRF, consisting of peptides homologous from the amino terminus of 44, 40 and 37 amino acids, were isolated.

The 44 amino acid amidated form of GRF is considered to be the parent molecule. A wide variety of synthetic analogs have been produced. They consist of biologically active fragments of the original polypeptide which incorporate various amino acid substitutions. The changes have been specifically engineered to often yield synthetic analogs with biological properties superior to those of the parent molecule. Generally, linear peptides are very flexible molecules and lack a well-defined conformation. Each amino acid in a linear peptide is exposed to the surrounding milieau resulting in greater susceptibility to enzymatic and chemical degradation.

Accordingly, it is desirable to develop GRF analogs which exhibit maximum biological activity in terms of, for example, potency, effectiveness, and stability together with resistance to enzymatic, non-enzymatic and chemical degradation, deamidation, and oxidation.

SUMMARY OF THE INVENTION

The present invention relates to compounds having a sequence of from about twenty-nine (29) to about forty-four (44) amino acids (SEQ ID NO: 6) wherein Xaa at position 1 is His, 3-MeHis, desNH$_2$His, Tyr, or desNH$_2$Tyr; Xaa at position 2 is Val, Leu, lle, Ala, D-Ala, N-methyl-D-Ala, Gly, Nle, or Nval; Xaa at position 8 is Gln, Ser or Thr; Xaa at position 15 is Ala or Leu; Xaa at position 27 is Met, Nle, or Leu; Xaa at position 28 is Ser or Asn; Xaa at position 29 is an amino acid sequence (SEQ ID NO: 7) or fragments thereof where the fragment is reduced in number by one to fifteen amino acid residues from the carboxyl-terminus, where the carboxyl-terminus can be the free carboxylic acid or the corresponding amide, and the pharmaceutically acceptable acid or base addition salts thereof.

Pharmaceutical compositions in accordance with the invention include such analogs which are between twenty-nine (29) and forty-four (44) residues in length dispersed in a pharmaceutically or veterinary acceptable liquid or solid carrier. Such pharmaceutical compositions can be used in clinical medicine, both human and veterinary, for administration for therapeutic and/or diagnostic purposes. Moreover, they can be used to promote the growth of warm and cold-blooded animals. They can also be used to treat growth related disorders and improve growth performance in warm and cold-blooded animals.

The GRF peptides of this invention are useful in methods for stimulating the release of growth hormone from the pituitary for use in the treatments described above.

DETAILED DESCRIPTION OF THE INVENTION

As used herein, the term "GRF" means human growth hormone releasing factor, a polypeptide having a sequence of 44 amino acids (SEQ ID NO: 1) (*Science*, 281, 585, Nov. 5, 1982) or biologically active fragments having at least the first 29 amino acids of the full polypeptide and displaying growth hormone releasing activity. In accordance with conventional representation, the amino group at the N-terminus appears to the left and the carboxyl group or carboxyl terminus at the C-terminus to the right. Amino acid is taken to mean one of the naturally occurring amino acids typically found in proteins comprising Gly, Ala, Val, Leu, Ile, Ser, Thr, Lys, Arg, Asp, Asn, Glu, Gln, Cys, Met, Phe, Tyr, Pro, Trp, and His. Nle means norleucine; Nval means norvaline. Where the amino acid residue has an isomeric form, it is the L-form of the amino acid that is represented unless otherwise expressly indicated. The suffixes "OH" and "NH$_2$" following "SEQ ID NO: #" (where # is the sequence number) refer to the free carboxylic acid and free amide forms of the compound, respectively, at the C-terminus. In the event neither suffix is used, the expression is intended to encompass both forms.

The term "Boc-SEQ ID NO: #-PAM resin" refers to a protected sequence of SEQ ID NO: # where Boc protects the amino group at the N-terminus and PAM-resin protects the C-terminus. The compounds can encompass the free carboxylic acid form or the amide form. Analogs of GRF are indicated by setting forth the substituted amino acid in brackets before "GRF"; for example, "[His$^1$,Ala$^{15}$]-GRF" indicates a polypeptide having an amino acid sequence corresponding to GRF in which a histidine residue has been substituted for the tyrosine residue at position 1 and an alanine residue has been substituted for the glycine residue at position 15. Numbers in parentheses following "GRF" indicate fragments of the full polypeptide by giving the position numbers of the amino acid residues; for example, GRF (1–29) indicates a fragment having the first 29 amino acids of the full sequence.

The invention relates to compounds having a sequence (SEQ ID NO: 6) wherein Xaa at position 1 is His, 3-MeHis, desNH$_2$His, Tyr, or desNH$_2$Tyr; Xaa at position 2 is Val, Leu, Ile, Ala, D-Ala, N-methyl-D-Ala, Gly, Nle or Nval; Xaa at position 8 is Gln, Ser or Thr; Xaa at position 15 is Ala or Leu; Xaa at position 27 is Met, Nle, or Leu; Xaa at position 28 is Ser or Asn; Xaa at position 29 is an amino acid sequence (SEQ ID NO:7) or fragments thereof where the fragment is reduced in number by one to fifteen amino acid residues from the carboxyl-terminus, where the carboxyl-terminus can be the free carboxylic acid or the corresponding amide, and the pharmaceutically acceptable acid or base addition salts thereof.

Pharmaceutical compositions in accordance with the invention include such analogs which are between twenty-nine (29) and forty-four (44) residues in length dispersed in a pharmaceutically or veterinary acceptable liquid or solid carrier. Such pharmaceutical compositions can be used in clinical medicine, both human and veterinary, for administration for therapeutic and/or diagnostic purposes. Moreover, they can be used to promote the growth of warm and cold-blooded animals as discussed above.

This invention is based on the discovery that the asparagine at position 8 and the glycine residue at position 15 of the GRF molecule, together with the tyrosine residue at position 1 and/or the alanine residue at position 2, can be replaced by a different appropriately selected amino acid producing a GRF analog having resistance to the formation of biologically inactive GRF analogs and enhanced biological potency for stimulating the release of growth hormone from the pituitary. It was found that replacing the asparagine residue at position 8 with a different appropriately selected amino acid prevents the slow deamidation of asparagine to the biologically inactive isoaspartic acid, especially at physiological pH (about 7.4). Additionally, the methionine residue at position 27 and/or the serine residue at position 28 can also be replaced in the same manner, also producing a GRF analog having enhanced biological potency. It was also found that replacing the methionine residue at position 27 with a different appropriately selected amino acid prevents the oxidation of methionine to methionine sulfoxide.

Various methods well known in the art may be used to select a particular amino acid for substitution in GRF at a particular position. One such method is to select a substitute amino acid so as to enhance the amphiphilic character and helical structure of the resulting polypeptide as demonstrated by helicity and hydropathicity analysis. The resultant peptides may bind more efficiently to the receptor and may be more stable to proteolytic breakdown thereby enhancing biological potency. Helicity and hydropathicity analyses are done by conventional methods known in the art.

In accordance with the invention substitutions of appropriately selected amino acid residues at positions 8 and 15 of the GRF molecule, together with substitutions of appropriately selected amino acid residues at positions 1 and/or 2, have enhanced biological activity and enzyme resistance. Additional substitutions of appropriately selected amino acid residues at positions 27 and/or 28 of the GRF molecule, concomitant to the substitution at the 8 and 15 positions together with the 1 and/or 2 positions, produce a multisubstituted GRF analog yielding peptides having increased biological potency in effecting the release of growth hormone by the pituitary. Selected amino acids for substitution at the appropriately selected positions include but are not limited to tyrosine, desNH$_2$tyrosine, alanine, D-alanine, leucine, isoleucine, methionine, valine, asparagine, serine, norleucine, histidine, desNH$_2$histidine, and 3-methylhistidine.

Further, the acid or amide of the 29 amino acid GRF molecule or a GRF analog greater than about 29 amino acids and less than 44 amino acids in length in addition to the substitution at the positions discussed above have enhanced biological activity and increased enzyme resistance.

Preferable fragments of SEQ ID NO: 7 include Arg, the first amino acid residue of SEQ ID NO: 7 and Arg-Gln-Gln-Gly, the first four amino acid residues of SEQ ID NO: 7.

Representative compounds of the present invention include:

SEQ ID NO: 8-NH$_2$, where Xaa$^1$ is desNH$_2$Tyr and Xaa$^2$ is D-Ala;

SEQ ID NO: 9-NH$_2$, where Xaa$^1$ is desNH$_2$Tyr and Xaa$^2$ is D-Ala;

SEQ ID NO: 10-NH$_2$, where Xaa$^1$ is desNH$_2$Tyr and Xaa$^2$ is D-Ala Ala;

SEQ ID NO: 11-OH;

SEQ ID NO: 12-OH;

SEQ ID NO: 13-OH;

SEQ ID NO: 14-OH;

SEQ ID NO: 15-OH;

SEQ ID NO: 16-OH;

SEQ ID NO: 17-OH where Xaa$^2$ is D-Ala;

SEQ ID NO: 18-OH;
SEQ ID NO: 19-OH;
SEQ ID NO: 20-OH;
SEQ ID NO: 21-OH;
SEQ ID NO: 22-OH;
SEQ ID NO: 23-OH;
SEQ ID NO: 24-OH, where Xaa$^1$ is desNH$_2$Tyr; and
SEQ ID NO: 31-OH, where Xaa$^1$ is desNH$_2$Tyr and Xaa$^2$ is D-Ala.

Although the modifications described are for the sequence comprising human growth hormone releasing factor, hGRF, similar modifications may be made to porcine growth hormone releasing factor, pGRF; bovine growth hormone releasing factor, bGRF; ovine growth hormone releasing factor, oGRF; and caprine growth hormone releasing factor, cGRF.

The polypeptides of this invention can be prepared by many procedures including, but not limited to, recombinant DNA methods, solid phase peptide synthesis techniques, or solution phase peptide synthesis techniques.

Using known techniques of DNA recombination, a DNA sequence containing the structural code for GRF could be inserted into a replicable expression vehicle under the control of appropriate control elements including a promoter-operator sequence and a sequence coding for a ribosome binding site. The expression vehicle would then be used to transform a host microorganism, such as a bacterium, which would be grown up and subjected to conditions under which it would express GRF. It will be recognized by those of ordinary skill in the art that in the present stated technology only natural amino acids can be introduced by recombinant methods. In those instances where non-naturally occurring amino acids are substituted in the GRF analogs, recombinant DNA techniques can be utilized to prepare the peptide containing the natural amino acid residues which could then be coupled with fragments containing non-naturally occurring amino acids by procedures well known in the art.

Peptides may be prepared using solid phase synthesis, such as that described by Merrifield, *J. Am. Chem. Soc.*, 8, 2149 (1963), although other equivalent chemical syntheses known to one of ordinary skill may be used. Solid phase synthesis is commenced from the C-terminal end of the peptide by coupling a protected amino acid via a benzyl ester linkage to a chloromethylated resin or a hydroxymethyl resin or via an amide bond to a benzhydrylamine (BHA) resin or methylbenzhydrylamine (MBHA) resin. The resins are available commercially and their preparation is known by one of ordinary skill in the art.

The acid form of the novel analogs may be prepared by the solid phase peptide synthesis procedure using a benzyl ester-resin or phenylacetamidomethyl-resin as a solid support. The polypeptide may be purified by preparative high performance liquid chromatography (HPLC) and then shown to be homogeneous by analytical HPLC, isoelectric focusing or high voltage thin layer electrophoresis. Amino acid analysis may be performed to confirm the expected amino acid composition. The corresponding amides may be produced by using benzhydrylamine or methylbenzhydrylamine resin as the solid support for solid phase peptide synthesis. Those skilled in the art will recognize that when the BHA or MBHA resin is used, treatment with anhydrous HF to remove the polypeptide from the solid support results in a polypeptide having a terminal amide group.

The C-terminal amino acid, for example, Arg, is protected at the N$^\alpha$-amino and side chain guanidino positions by appropriately selected protecting groups, in the case of Arg by t-butyloxycarbonyl (Boc) and p-toluenesulfonyl (Tos), respectively. The Boc-Arg(Tos)-OH can be first coupled to the benzhydrylamine resin using dicyclohexyl-carbodiimide (DCC) at about 25° C. for 2 hours with stirring. Following the coupling of the Boc protected amino acid to the resin support, the α-amino protecting group is removed, using trifluoroacetic acid (TFA) in methylene chloride or TFA alone. The deprotection is carried out at a temperature between about 0° C. and room temperature.

After removal of the α-amino protecting group, the remaining Boc-protected amino acids are coupled stepwise in the desired order or as an alternative to adding each amino acid separately in the synthesis, some may be activated prior to its addition to the solid phase synthesizer. The selection of an appropriate coupling reagent is known to one of ordinary skill in the art. Particularly suitable is DCC.

Each protected amino acid is introduced in the desired amino acid sequence into the solid phase reactor in excess, and the coupling may be carried out in a medium of dimethylformamide (DMF) or methylene chloride (CH$_2$Cl$_2$) or mixtures thereof. In cases where incomplete coupling occurs, the coupling procedure is repeated before removal of the N$^\alpha$-amino protecting group prior to the coupling of the next amino acid. The success of the coupling reaction at each stage of synthesis may be monitored by procedures well known in the art. A preferred method of monitoring the synthesis is by the ninhydrin reaction. The coupling reactions can be performed automatically, for example, using a Vega Model 1000, a Model 250 or Model 296 Peptide Synthesizer or Applied Biosystems Model 430A or 431A Peptide Synthesizer.

Cleavage of the peptide from the resin can be effected using procedures well known in peptide chemistry. Reaction with hydrogen fluoride in the presence of scavengers such as p-cresol and dimethylsulfide at 0° C. for 1 hour may be followed by a second reaction with hydrogen fluoride in the presence of p-cresol for 2 hours at 0° C.

Purification of the polypeptides of the invention can be effected using procedures well known in peptide chemistry. As previously indicated, the subject polypeptides may be purified using preparative HPLC; however, other known chromatographic procedures such as gel permeation, ion exchange and partition chromatography or countercurrent distribution can also be employed.

The polypeptides of this invention have growth hormone releasing activity. Pharmaceutical compositions in accordance with the invention include analogs of about 29 to about 44 amino acids in length, or a nontoxic salt of any of these, dispersed in a pharmaceutically or veterinarily acceptable liquid or solid carrier. Such pharmaceutical compositions can be used for therapeutic or diagnostic purposes in clinical medicine, both human and veterinary. For example, they are useful in the treatment of growth-related disorders such as hypopituitary dwarfism and diabetes resulting from abnormalities in growth hormone production. Furthermore they can also be used to stimulate the growth or enhance feed efficiency of animals raised for meat production, to improve the quality of meat, to enhance milk production, and to stimulate egg production. In addition, they can be used in aquiculture, for example, for raising or accelerating the growth of fish and other cold blooded marine animals.

Appropriate dosages of the polypeptides of the invention to be administered will vary somewhat depending on the individual subject and the condition being treated. The skilled worker will be able to determine appropriate dosages based on the known circulating levels of growth hormone associated with normal growth and the growth hormone releasing activity of the polypeptide.

Compounds of this invention have increased potencies in vitro that are at least 2.5 times greater than that of GRF-(1–44)-NH$_2$ (SEQ ID NO: 1-NH$_2$). Thus, these analogs can be administered in significantly lower dosages than if growth hormone releasing factor were given for the same purpose. As is well known in the art, treatment of growth-related disorders will necessitate varying dosages from individual to individual depending upon the degree of insufficiency of growth hormone production. Generally, a dosage range of from about 0.04 μg/kg/day to about 30.0 μg/kg/day (subcutaneous) based on body weight of the subject may be used to stimulate release of growth hormone. The dosage employed to stimulate growth activity in livestock will be significantly higher (per kg. of subject weight) than the dosages employed to restore normal growth in cases of growth hormone deficiencies such as pituitary dwarfism in humans. In livestock generally a dosage in the range of from about 0.4 μg/kg/day to about 30 μg/kg/day subcutaneously may be used to stimulate release of growth hormone from the pituitary.

Thus, there is provided in accordance with this invention a method of treating growth-related disorders characterized by insufficient production of growth hormone which comprises administering an amount of the analogs of this invention sufficient to stimulate the production of growth hormone to levels associated with normal growth.

Normal levels of growth hormone vary considerably among individuals and, for any given individual, levels of circulating growth hormone vary considerably during the course of a day. In adult humans, normal serum levels of growth hormone have been reported to vary from about 0 to about 10 nanograms/ml. In children, normal serum levels of growth hormone have been reported to vary from about 0 to about 20 nanograms/ml.

In order to treat hypopituitary dwarfism effectively with the described analogs, treatment is administered as early as possible following diagnosis of growth hormone deficiency. Treatment can begin as early as 2 to 3 years of age and can extend up to about 18 to 19 years of age and, in some individual cases, up to about 25 years.

There is also provided a method of increasing the growth rate of animals by administering an amount of the inventive GRF analog sufficient to stimulate the production of growth hormone at a level greater than that associated with normal growth.

The polypeptides of the invention can be administered in the form of human or veterinary pharmaceutical compositions which can be prepared by conventional pharmaceutical formulation techniques. Compositions suitable for oral, intravenous, subcutaneous, intramuscular, intraperitoneal or intranasal administration may be employed. A suitable dosage form for pharmaceutical use is from about 0.01 to about 0.5 mg of the compound of the invention, which may be lyophilized for reconstitution with sterile water or saline. The composition should be maintained at a pH below about 8.0 in order to maintain the stability of the analog. Serum albumin from the species being treated (for example, human serum albumin in the case of humans, bovine serum albumin in the case of cows and so forth) may also be present together with other known pharmaceutical adjuvants.

The polypeptides of this invention describe GRF analogs which possess, among other properties, enhanced stability to enzymatic (dipeptidylpeptidase-IV) degradation and enhanced biological activity.

The following examples are presented in order to illustrate the practice of this invention and are not to be construed as limiting the scope of the invention in any way. Unless otherwise stated, all parts and percents are given by weight and all temperatures are in degrees centigrade. Unless otherwise stated (as in the present tense), the examples below have been carried out as actually described.

In the examples, optically active protected amino acids in the L-configuration were employed except where specifically noted. The protected amino acids were examined by thin layer chromatography on silica gel G plates and developed with chlorine-TDM. Amino acid analysis was performed on a Waters Amino Acid Analyzer.

The following abbreviations are used in the examples to indicate various protecting groups and reagents.

Boc=t-butyloxycarbonyl

Tos=p-toluenesulfonyl

DCC=dicyclohexylcarbodiimide

BHA=benzhydrylamine

DMF=dimethylformamide

TFA=trifluoroacetic acid

EtOAc=ethyl acetate

CH$_2$Cl$_2$=methylene chloride

Bzl=benzyl cHex=cyclohexyl

Cz=2-chlorobenzyloxycarbonyl

HOBt=hydroxybenzotriazole

TDM=4,4'-tetramethyldiaminodiphenylmethane

Dcb=2,6-dichlorobenzyl

BOP=benzotriazol-1-yloxytris(dimethylamino) phosphonium hexafluoropho

PAM=phenylacetamidomethyl

The analogs of this invention were prepared by sequential coupling of amino acids by a manual mode or by employing commercially available automated solid phase peptide synthesizers (for example, Vega Model 1000, Model 250 or Model 296 Peptide Synthesizer or the Applied Biosystems Model 431A or 430A Peptide Synthesizer). N$^\alpha$-Boc-amino acids were used in the synthesis.

Trifunctional amino acids were protected as

Nα-Boc-Arg(Tos)-OH, Nα-Boc-His(Tos)-OH,

Nα-Boc-Lys(2Cz)-OH, Nα-Boc-Ser(Bzl)-OH,

Nα-Boc-Thr(Bzl)-OH, Nα-Boc-Asp(cHex)-OH, and Nα-Boc-Tyr(Dcb)-OH. Unless otherwise stated, the free carboxylic acid form of the GRF compound was formed in the examples below. The examples, unless otherwise stated, were carried out as stated. Temperatures are in degrees celsius.

EXAMPLE 1

PREPARATION OF SEQ ID NO: 26-OH

Boc-Gly-PAM-resin (Bachem, 50 g, 0.76 mmol/g) was charged into the reaction vessel of a Vega 296 Peptide Synthesizer and solid phase peptide synthesis (SPPS) performed by the DCC procedure for a total of 9 cycles to give protected Boc-SEQ ID NO: 25-PAM-resin, {Boc-[Leu$^{27}$, Asn$^{28}$]-GRF(23–32)-PAM-resin}. A 10 g aliquot of the protected Boc-SEQ ID NO: 25-PAM-resin was subjected to 14 additional cycles of SPPS to give 13.8 g of protected Boc-SEQ ID NO: 26-PAM-resin {Boc-[Ala$^{15}$, Leu$^{27}$, Asn$^{28}$]-GRF(9–32)-PAM-resin}. An aliquot of protected Boc-SEQ ID NO: 26-PAM-resin was treated with anhydrous HF (containing 10% propanethiol) for 2h at 0°. The HF was evaporated at 0° (high-vac; CaO trap), and the crude peptide resin mixture was triturated with EtOAc, extracted with TFA and filtered. The filtrate was evaporated to dryness and the residue triturated with anhydrous ether and dried to give 100 mg of crude compound SEQ ID NO: 26-OH.

The crude material (100 mg) was dissolved in 20 mL of 0.1% TFA/$H_2O$, filtered and loaded onto a prep-pak YMC-Basic HPLC column (4.8×30 cm). The column was eluted with (A) $H_2O$ (0.1% TFA)—(B) $CH_3CN$ (0.1% TFA) in a linear gradient from 20% (B) to 45% (B) in 90 minutes with a flow rate of 50 mL/min. Fractions were collected (0.5 min/fraction) and aliquots analyzed by the analytical HPLC system: (A) 0.1$\underline{M}$ $NaClO_4$ (pH 2.5)—(B) $CH_3CN$; 40% (B) to 55% (B) in 20 min at 1 mL/min, 0.2 AUFS, 206 nm. Column: Lichrosorb RP-8, 5 micron. The product emerged in fractions 184–185, and were combined, evaporated and lyophilized to give 13 mg of SEQ ID NO: 26-OH.

The product was shown to be homogeneous by analytical HPLC and gave the expected amino acid composition after acid hydrolysis [Hydrolysis: 6$\underline{N}$ HCl containing 1% thioglycolic acid (TGA); 150° C.; 1h]: Ser 1.95 (2), Tyr 1.05 (1), [6$\underline{N}$ HCl (1% TGA), 110° C.; 72h)]: Asp 2.04 (2) Glu 4.11 (4), Gly 1.23 (1), Ala 2.02 (2), Val 0.97 (1), lle 0.98 (1), Leu 5.03 (5), Lys 2.02 (2), Arg 2.82 (3). Confirmation of structure was provided by FAB mass spectrometry. Calcd: $(M+H)^+$ 2800.3. Found: 2800.4

EXAMPLE 2

PREPARATION OF SEQ ID NO: 14-OH

A 1 g portion of protected Boc-SEQ ID NO: 26-PAM-resin (from Example 1) was subjected to 8 additional cycles of SPPS using BOP procedure to yield 1.5 g of protected Boc-SEQ ID NO: 14-PAM-resin.

The protected Boc-SEQ ID NO: 14-PAM-resin was cleaved with anhydrous HF (as in Example 1) to give 781 mg of crude peptide which was dissolved in 20 mL of 0.1% TFA/$H_2O$, filtered and loaded onto a Prep-Pak YMC-Basic column (4.8×30 cm). The column was eluted with (A) $H_2O$ (0.1% TFA)— (B) $CH_3CN$ (0.1% TFA) in a linear gradient mode from 20% (B)—45% (B) in 90 min. with a flow rate of 50 mL/min. Fractions were collected every 0.5 min. and analyzed by the analytical HPLC system. Fractions containing semi-pure product were combined, evaporated and lyophilized.

The semi-pure material was dissolved in 0.1% TFA/$H_2O$ and loaded onto a 2.2×25 cm Nucleosil C-18 column. The column was eluted with (A) $H_2O$ (0.1% TFA)—(B) $CH_3CN$ (0.1% TFA) in a linear gradient mode from 25% (B) to 40% (B) in 90 min with a flow rate of 15 mL/min. Fractions were collected every minute and aliquots analyzed by the analytical HPLC system. The product emerged in fractions 43–53 which were combined, evaporated and lyophilized to give 75 mg of pure SEQ ID NO: 14-OH.

The product was shown to be homogeneous by analytical HPLC and gave the expected amino acid composition after hydrolysis (6$\underline{N}$ HCl-1% TGA; 150° C.; 1h): Thr 0.99 (1), Ser 1.93 (2), Tyr 1.08 (1). (6$\underline{N}$ HCl-1% TGA; 110° C.; 72h): Asp 3.07 (3), Glu 5.04 (5), Gly 1.11 (1.0), Ala 3.10 (3), Val 1.92 (2), lle 1.87 (2), Leu 4.90 (5), Phe 0.98 (1), His 1.00 (1), Lys 2.00 (2), Arg 2.99 (3). Confirmation of structure was provided by FAB mass spectrometry. Calcd: $(M+H)^+$3712.3. Found: 3711.5.

EXAMPLE 3

PREPARATION OF SEQ ID NO: 12-OH

A 2.2 g portion of protected Boc-SEQ ID NO: 26-PAM-resin (from Example 1) was subjected to 6 cycles of SPPS, as in Example 2, to give 2.1 g of protected [Boc-SEQ ID NO: 27-PAM-resin, {Boc-[Thr$^8$, Ala$^{15}$, Leu$^{27}$, Asn$^{28}$]-GRF (3–32)-PAM-resin}. A 1.0 g portion of protected Boc-SEQ ID NO: 27-PAM-resin was subjected to two additional cycles of SPPS to give protected Boc-SEQ ID NO: 12-PAM-resin. An aliquot (0.6 g) was cleaved with anhydrous HF to give 320 mg of crude peptide. HPLC purification (as in Example 2) gave 20 mg of pure SEQ ID NO: 12–OH.

The product was shown to be homogeneous by analytical HPLC and gave the expected amino acid composition after acid hydrolysis (6$\underline{N}$ HCl-1% TGA; 110° C.; 24h): Asp 3.03 (3), Thr 1.92 (2), Ser 1.91 (2), Glu 4.30 (4), Gly 1.01 (1), Ala 3.03 (3), Tyr 1.00 (1), His 0.98 (1), Lys 1.97 (2), Arg 2.88 (3). (6$\underline{N}$ HCl-1% TGA; 110° C.; 72h): Val 1.98 (2), lle 1.95 (2), Leu 5.06 (5), Phe 1.00 (1). Confirmation of structure was provided by FAB mass spectrometry. Calcd: $(M+H)^+$ 3685.2. Found: 3684.5.

EXAMPLE 4

PREPARATION OF SEQ ID NO: 16-OH

A 2.2 g portion of protected Boc-SEQ ID NO: 26-PAM-resin (from Example 1) was subjected to 6 cycles of SPPS, as in Example 2, to give 2.1 g of protected Boc-SEQ ID NO: 28-PAM-resin, {Boc-[Ser$^8$, Ala$^{15}$, Leu$^{27}$, Asn$^{28}$]-GRF (3–32)-PAM-resin}. A 1.0 g aliquot of protected Boc-SEQ ID NO: 28-PAM-resin was subjected to two additional cycles of SPPS and the resultant protected peptide resin (0.94 g) cleaved with HF to give 0.53 g of crude peptide which was purified as in Example 2. The product (37 mg) was shown to be homogeneous by analytical HPLC and gave the expected amino acid composition after acid hydrolysis (6$\underline{N}$ HCl-1% TGA; 110° C.; 24h): Asp 2.08 (2), Thr 0.98 (1), Ser 3.78 (4), Glu 4.39 (4), Gly 1.09 (1), Ala 3.13 (3), Val 1.80 (2), lle 1.81 (2), Leu 5.08 (5), Tyr 1.02 (1), Phe 0.91 (1) His 0.99 (1), Lys 2.00 (2), Arg 2.94 (3). Confirmation of structure was provided by FAB mass spectrometry. Calcd: $(M+H)^+$3671.2. Found: 3670.7.

EXAMPLE 5

PREPARATION OF SEQ ID NO: 29-OH

Boc-Gly-PAM-resin (10 g; 0.76 mmol g; 7.6 mmol) was charged into a reaction vessel and 23 cycles of SPPS carried out in a manual mode to yield 17.2 g of protected Boc-SEQ ID NO: 29-PAM-resin, {Boc -[Ala$^{15}$, Leu$^{27}$]-GRF(9–32)-PAM-resin}. A 200 mg aliquot was cleaved with HF, purified by HPLC on a Nucleosil C-18, 10 micron 300 Å column (2.2×25 cm) to give 2.5 mg of pure SEQ ID NO: 29-OH.

The product was shown to be essentially homogeneous by analytical HPLC and gave the expected amino acid composition after acid hydrolysis (6$\underline{N}$ HCl-1% TGA; 150°; 1h): Ser 3.00 (3), Tyr 1.00 (1). (6$\underline{N}$ HCl-1% TGA; 110°; 24h): Asp 1.10 (1), Glu 4.10 (4), Gly 1.03 (1), Ala 1.87 (2), lle 0.93 (1), Leu 4.81 (5), Lys 2.03 (2), Arg 3.05 (3). (6$\underline{N}$ HCl-1% TGA; 110° C.; 72h): Ala 2.05 (2), Val 0.95 (1). Confirmation of structure was provided by FAB mass spectroscopy: Calcd: $(M+H)^+$2773.3. Found: 2773.3.

EXAMPLE 6

PREPARATION OF SEQ ID NO: 13-OH

A 1.5 g portion of protected Boc-SEQ ID NO: 29-PAM-resin (from Example 5) was subjected to 8 additional cycles of SPPS to give protected Boc-SEQ ID NO: 13-PAM-resin. The protected peptide resin was cleaved with anhydrous HF to give 0.83 g of crude material which was purified by HPLC (as in Example 2). Yield: 17 mg. The product was shown to be essentially homogeneous by analytical HPLC and gave the expected composition after acid hydrolysis (6N HCl-1% TGA; 110° C.; 24h): Thr 1.04 (1), Ser 2.76 (3), Tyr 0.96 (1). (6N HCl-1% TGA; 110° C.; 72h): Asp 1.92 (2); Glu 4.89 (5), Gly 1.00 (1), Ala 2.88 (3), Val 1.82 (2), Ile 1.82 (2), Leu 4.92 (5), Phe 0.92 (1), His 0.96 (1), Lys 1.97 (2), Arg 2.73 (3). Confirmation of structure was further provided by FAB mass spectrometry. Calcd: (M+H)$^+$ 3685.3. Found: 3685.7.

EXAMPLE 7

PREPARATION OF SEQ ID NO: 23-OH

A 0.5 g portion of protected Boc-SEQ ID NO: 30-PAM-resin, {Boc- [Gln$^8$, Ala$^{15}$, Leu$^{27}$]-GRF(3–32)-PAM-resin}, (an intermediate from Example 6) was subjected to 2 additional cycles of SPPS and the resultant protected peptide Boc-SEQ ID NO: 23-PAM-resin, (0.46 g) was,; cleaved with HF to give 284 mg of crude Boc-SEQ ID NO: 23-OH which was purified by HPLC (as in Example 1) to give 28 mg of product that was shown to be essentially homogeneous by analytical HPLC and gave the expected amino acid composition after acid hydrolysis (6N HCl-1% TGA; 150° C.; 1h): Thr 1.00 (1), Ser 2.89 (3), Tyr 1.10(1). (6N HCl-1% TGA; 110° C.; 72h): Asp 1.96 (2), Glu 5.19(5), Gly 1.05 (1), Ala 3.91 (4), Val 1.02 (1), Ile 1.88 (2), Leu 5.02 (5), Phe 0.89 (1), His 0.90 (1), Lys 2.07 (2), Arg 3.10 (3). Confirmation of structure was provided by FAB mass spectrometry. Calcd: (M+H)$^+$3657.2. Found: 3657.2.

EXAMPLE 8

PREPARATION OF SEQ ID NO: 17-OH where Xaa$^2$ is D-Ala

A 0.5 g portion of protected Boc-SEQ ID NO: 30-PAM-resin (intermediate from Example 6) was subjected to 2 additional cycles of SPPS to give 0.46 g protected Boc-SEQ ID NO: 17-PAM-resin where Xaa$^2$ is D-Ala. The protected peptide resin (0.46 g) was cleaved with HF to give 270 mg of crude SEQ ID NO: 17-OH where Xaa$^2$ is D-Ala which was purified by HPLC (as in Example 1) to yield 30 mg of product that was found to be essentially homogeneous by analytical HPLC and gave the expected amino acid composition after hydrolysis (6N HCl-1% TGA; 150° C.; 1h): Thr 0.97 (1), Ser 2.96 (3), Tyr 1.07 (1). (6N HCl-1% TGA; 110° C., 72h): Asp 2.00 (2), Glu 5.37 (5), Gly 1.05 (1), Ala 3.77 (4), Val 0.95 (1), Ile 1.88 (2), Leu 5.14 (5), Phe 0.85 (1), His 0.91 (1), Lys 1.96 (2), Arg 3.12 (3). Confirmation of structure was provided by FAB mass spectrometry. Calcd: (M+H)$^+$3657.2. Found: 3656.5.

EXAMPLE 9

PREPARATION OF SEQ ID NO: 31-OH where Xaa$^1$ is desNH$_2$Tyr and Xaa$^2$ is D-Ala A 0.5 g portion of protected Boc-SEQ ID NO: 30-PAM-resin (intermediate from Example 6) was subjected to 2 additional cycles of SPPS to give 0.44 g protected Boc-SEQ ID NO: 31-PAM-resin where Xaa$^1$ is desNH$_2$Tyr and Xaa$^2$ is D-Ala. The protected peptide resin was cleaved with HF to give 250 mg crude product which was purified by HPLC as in Example 1. The purified product, SEQ ID NO: 31-OH where Xaa$^1$ is desNH$_2$Tyr and Xaa$^2$ is D-Ala (40 mg) was shown to be essentially homogeneous by analytical HPLC and gave the expected amino acid composition after acid hydrolysis (6N HCl-1% TGA; 150° C.; 1h): Thr 1.04 (1), Ser 2.87 (3), Tyr 1.10 (1). (6N HCl-1% TGA; 110° C.; 24h): Asp 1.96, Glu 5.19 (5), Ala 3.99 (4), Val 0.93 (1), Leu 4.91 (5), Lys 2.01 (2), Arg 3.10 (3). (6N HCl-1% TGA; 110°0 C.; 72h): Gly 1.11 (1), Ile 1.93 (2), Phe 0.96 (1). Confirmation of structure was provided by FAB mass spectrometry. Calcd: (M+H)$^+$3668.2. Found: 3668.0.

EXAMPLE 10

PREPARATION OF SEQ ID NO: 24-OH where Xaa$^1$ is desNH$_2$Tyr

A 0.5 g of protected Boc-SEQ ID NO: 30-PAM-resin (intermediate from Example 6) was subjected to 2 additional cycles of SPPS to give 0.43 g of protected Boc-SEQ ID NO: 21-PAM-resin where Xaa$^1$ is desNH$_2$Tyr. The protected peptide resin was cleaved with HF to give 224 mg of crude material which was purified by HPLC. The product, SEQ ID NO: 24-OH where Xaa$^1$ is desNH$_2$Tyr (yield: 25 mg) was shown to be essentially homogeneous by analytical HPLC and gave the expected amino acid composition after acid hydrolysis (6N HCl-1% TGA; 150° C.; 1h): Thr 1.00 (1), Ser 2.93 (3), Tyr 1.07 (1). (6N HCl-1% TGA; 110° C.; 24h): Asp 2.00 (2), Glu 5.18 (5), Gly 1.07 (1), Ala 3.08 (3), Val 1.95 (2), Ile 1.83 (2), Leu 5.01 (5), Phe 0.84 (1), Lys 2.03 (2), Arg 3.00 (3). Confirmation of structure was provided by FAB mass spectrometry. Calcd: (M+H)$^+$3696.3. Found: 3695.9.

EXAMPLE 11

PREPARATION OF SEQ ID NO: 19-OH

A 0.5 g portion of protected Boc-SEQ ID NO: 30-PAM-resin (intermediate from Example 6) was subjected to 2 additional cycles of SPPS. The peptide resin (0.48 g) was treated with HF and the crude peptide purified by HPLC to give 33 mg of pure SEQ ID NO: 19-OH.

The product was shown to be essentially homogeneous by analytical HPLC and gave the expected amino acid composition after acid hydrolysis (6N HCl-1% TGA; 150° C.; 1h): Thr 0.99 (1), Ser 2.96 (3), Tyr 2.04 (2). (6N HCl-1% TGA; 110° C., 24h): Asp 2.07 (2), Glu 5.10 (5), Gly 1.11 (1), Ala 3.10 (3), Val 1.77 (2), Ile 1.78 (2), Leu 5.03 (5), Phe 0.91 (1), Lys 2.09 (2), Arg 3.01 (3). Confirmation of structure was provided by FAB mass spectrometry. Calcd: (M+H)$^+$3710.3. Found: 3709.6.

EXAMPLE 12

PREPARATION OF SEQ ID NO: 11-OH

A 2.0 g portion of protected Boc-SEQ ID NO: 29-PAM-resin (from Example 5) was subjected to 6 cycles of SPPS to give 2 g of protected Boc-SEQ ID NO: 32-PAM-resin, {Boc-[Thr$^8$, Ala$^{15}$, Leu$^{27}$]-GRF(3–32)-PAM-resin}. A 0.93 g portion was subjected to 2 additional cycles of SPPS and the protected peptide resin cleaved with HF and purified by HPLC to give 29 mg of SEQ ID NO: 11-OH.

The product was shown to be essentially homogeneous by analytical HPLC and gave the expected amino acid composition after acid hydrolysis: (6N HCl-1% TGA; 110° C.; 24h): Asp 2.05 (2), Thr 1.85 (2), Ser 2.80 (3), Glu 4.40 (4), Gly 1.09 (1), Ala 3.01 (3), Leu 5.05 (5), Tyr 0.98 (1), His 0.95 (1), Lys 1.99 (2), Arg 2.90 (3). (6N HCl 110° C.; 72h):

Val 2.00 (2), lle 2.00 (2), Phe 1.00 (1). Confirmation of structure was provided by FAB Mass Spectrometry. Calcd: $(M+H)^+ 3671.2$. Found: 3670.7.

EXAMPLE 13

PREPARATION OF SEQ ID NO: 15-OH

A 2.0 g portion of protected Boc-SEQ ID NO: 29-PAM-resin (from Example 5) was subjected to 9 additional cycles of SPPS to give 2.0 g of protected Boc-SEQ ID NO: 15-PAM-resin. A 1 g portion was cleaved with HF to give 540 mg of crude peptide which was purified by HPLC to give 101 mg of SEQ ID NO: 15-OH.

The product was shown to be essentially homogeneous by analytical HPLC and gave the expected amino acid composition after acid hydrolysis (6$\underline{N}$ HCl-1% TGA; 110°0 C.; 24h): Asp 3.09 (3), Thr 0.98 (1), Ser 2.87 (3), Glu 4.45 (4), Gly 1.09 (1), Ala 3.07 (3), Leu 5.04 (5), Tyr 1.02 (1), His 0.98 (1), Lys 2.01 (2), Arg 3.02 (3). (6$\underline{N}$ HCl-1% TGA; 110° C.; 72h): Val 1.99 (2), lle 1.94 (2), Phe 1.00 (1). Confirmation of structure was provided by FAB mass spectrometry. Calcd: $(M+H)^+ 3644.2$. Found: 3643.5.

EXAMPLE 14

PREPARATION OF SEQ ID NO: 8-NH$_2$ where Xaa$^1$ is desNH$_2$Tyr and Xaa$^2$ is D-Ala Boc-Arg(Tos)-benzhydrylamine resin (10 g, 0.45 mmol/g) was charged into a 250 mL reaction vessel clamped to a Model S-500 shaker equipped with an RD-20 shaker head. Solid phase peptide synthesis was performed manually by the DCC/HOBt and BOP procedures for a total of 20 cycles to give 20.5 g of protected Boc-SEQ ID NO: 33-BHA-resin, {Boc-[Ala$^{15}$]-GRF(9–29)-BHA resin} A 1.5 g portion of the peptide-resin was removed, charged into a reaction vessel and solid phase synthesis continued for an additional 8 cycles to give protected Boc- SEQ ID NO: 8-BHA-resin where Xaa$^1$ is desNH$_2$Tyr and Xaa$^2$ is D-Ala (1.4 g). A portion of the protected peptide resin (800 mg) was treated with anhydrous liquid HF using the modified conditions of Tam et al. [*Tetrahedron Lett.*, 23, 2939–2942 (1982)]; p-cresol (10%): dimethylsulfide (65%): HF (25%) [total volume: 10 mL] at 0° for 1 hr and evaporated. This was followed by another reaction with p-cresol (10%): HF (90%) [Total volume: 10 mL] at 0° for 2 hrs. The HF was evaporated at 0° (high-vac, CaO trap) and the crude peptide and resin mixture triturated with EtOAc, ether and extracted with TFA, filtered and dried to give 400 mg crude peptide.

This crude material was dissolved in 20 mL of 0.1% TFA/H$_2$O, filtered (0.45 $\mu$ Type HA Millipore filter) and loaded onto a Prep-Pak YMC basic column (4.8×30 cm). The column was eluted with (A) H$_2$O (0.1% TFA)—(B) CH$_3$CN (0.1% TFA) in a linear gradient going from 20% (B) to 50% (B) in 90 minutes with a flow rate of 50 mL/min. Fractions were collected (0.5 min/fraction) and aliquots analyzed by the analytical HPLC system: (A) 0.1$\underline{M}$ NaClO$_4$ (pH 2.5)—(B) CH$_3$CN; 35% (B) to 55% (B) in 20 min at 1 mL/min. Column: Lichrosorb RP-8 (5$\mu$). The product which emerged in fractions 78–80 was combined, evaporated and lyophilized to give 10 mg of pure SEQ ID NO: 8-NH$_2$ where Xaa$^1$ is desNH$_2$Tyr and Xaa$^2$ is D-Ala. Fractions 73–77 and 81–84 were also pooled, evaporated and lyophilized to give 39 mg of semi-pure product.

The purified product was shown to be homogeneous by analytical HPLC and gave the expected amino acid composition (Hydrolysis: 6$\underline{N}$ HCl, 110° C., 24h): Asp 1.90 (2), Thr 1.73 (2), Ser 3.05 (3), Glu 2.20 (2), Ala 4.06 (4), Val 0.80 (1), Met 1.02 (1), lle 1.77 (2), Leu 4.25 (4), Tyr 0.94 (1), Phe 0.83 (1), Lys 1.89 (2), Arg 3.21 (3). Confirmation of structure was provided by FAB mass spectroscopy. Calcd: $(M+H)^+$ 3343.9. Found: 3345.1.

EXAMPLE 15

PREPARATION OF SEQ ID NO: 9-NH$_2$ where Xaa$^1$ is desNH$_2$Tyr and Xaa$^2$ is D-Ala A 1.5 g portion of protected Boc-SEQ ID NO: 33-BHA-resin (intermediate from Example 14) was subjected to 8 cycles of solid phase synthesis to give 1.4 g of protected Boc-SEQ ID NO: 9-BHA-resin where Xaa$^1$ is desNH$_2$Tyr and Xaa$^2$ is D-Ala. A 0.9 g portion was cleaved with anhydrous HF (as in Example 14) to give 495 mg of crude peptide which was purified (as in Example 14) and 42 mg of pure SEQ ID NO: 9-NH$_2$ where Xaa$^1$ is desNH$_2$Tyr and Xaa$^2$ is D-Ala was obtained.

The product was shown to be homogeneous by analytical HPLC and gave the expected amino acid composition (Hydrolysis: 6$\underline{N}$150° C., 1h): Thr 1.01 (1), Ser 3.99 (4), (6$\underline{N}$ HCl, 110° C., 24h): Asp 1.94 (1), Glu 2.03 (2), Ala 4.00 (4), Val 0.91 (1), Met 0.96 (1), lle 1.84 (2), Leu 4.04 (4), Tyr 1.00 (1), Phe 0.88 (1), Lys 1.93 (2), Arg 2.93 (3). Confirmation of structure was provided by FAB mass spectroscopy. Calcd: $(M+H)^+$ 3330.9. Found: 3332.1.

EXAMPLE 16

PREPARATION OF SEQ ID NO: 10-NH$_2$ where Xaa$^1$ is desNH$_2$Tyr and Xaa$^2$ is D-Ala A 1.5 g portion of protected Boc-SEQ ID NO: 33-BHA-resin (intermediate from Example 14) was subjected to 8 additional cycles of solid phase synthesis to give 1.05 g of protected Boc-SEQ ID NO: 10-BHA-resin where Xaa$^1$ is desNH$_2$Tyr and Xaa$^2$ is D-Ala. A 0.69 g portion was cleaved with anhydrous HF (as in Example 14) to give 495 mg of crude peptide which was purified as in Example 14 and 31 mg of pure SEQ ID NO: 10-NH$_2$ where Xaa$^1$ is desNH$_2$Tyr and Xaa$^2$ is D-Ala was obtained.

The product was shown to be homogeneous by analytical HPLC and gave the expected amino acid composition after acid hydrolysis (6N HCl, 110° C., 24h): Asp 1.96 (2), Thr 0.95 (1), Ser 3.01 (3), Glu 3.08 (3), Ala 4.10 (4), Val 0.85 (1), Met 1.00 (1), lle 1.80 (2), Leu 4.12 (4), Tyr 0.97 (1), Phe 0.87 (1), Lys 1.88 (2), Arg 3.14 (3). Confirmation of structure was provided by FAB mass spectroscopy. Calcd: $(M+H)^+$ 3371.0. Found: 3371.7.

EXAMPLE 17

SYNTHESIS OF SEQ ID NO: 37-OH

Boc-Gly-Pam-resin can be charged into a reaction vessel of an Applied Biosystems Model 430A Peptide Synthesizer and can be subjected to 31 cycles of solid phase peptide synthesis to give protected SEQ ID NO: 37-Pam-resin. The protected peptide-Pam-resin can be treated with HF as in Example 1 to yield crude SEQ ID No: 37-OH. A portion of this crude product can then be subjected to HPLC purification as in Example 2. The desired product emerging in several fractions can be combined, evaporated and lyophilized. The product can be shown to be homogeneous by analytical HPLC and confirmed by amino acid analysis and FAB mass spectrometry.

EXAMPLE 18

SYNTHESIS OF SEQ ID NO: 38-OH WHERE $Xaa^{27}$ is Nle

Boc-Gly-Pam-resin can be charged into a reaction vessel of an Applied Biosystems Model 430A Peptide Synthesizer and can be subjected to 31 cycles of solid phase peptide synthesis to give protected SEQ ID NO: 38-Pam-resin where $Xaa^{27}$ is Nle. The protected peptide can be treated with HF as in Example 1 to yield crude SEQ ID NO: 38-OH where $Xaa^{27}$ is Nle. A portion of this crude product can then be subjected to HPLC purification as in Example 2. The desired product emerging in several fractions can be combined, evaporated and lyophilized. The product can be shown to be homogeneous by analytical HPLC and confirmed by amino acid analysis and FAB mass spectrometry.

EXAMPLE 19

The biological activity of the novel peptides were compared with that of a synthetic standard of the natural sequence of GRF(1–44)-$NH_2$ (SEQ ID NO: 1-$NH_2$) which was isolated from a human pancreatic tumor of an individual suffering from acromegaly (Salk Institute standard hp-GRF-$NH_2$(NL-A-10)). The assay for biological activity, which is based on the ability to stimulate production of growth hormone in rat pituitary cells in tissue culture, was performed in the following manner.

Pituitaries from 30–40 male Sprague-Dawley rats (175 g) were removed aseptically after decapitation. The anterior lobes were collected, washed 3 times in sterile Hepes buffer (0.025M)(pH 7.35) and dispersed at 37° C. in 20–30 ml Hepes buffer (pH 7.35) containing collagenase (4 mg per ml) and Dispase (Protease grande II, 2 mg per ml). After gentle 80 min. vortexing and trituration by Pasteur pipette, the dispersed cells were separated by centrifugation (150×g, 4 min.) and re-suspended in Hepes buffer containing neuraminidase (4 mg/ml), and 200 mg/ml ethylenediaminetetraacetic acid (EDTA) disodium salt pH 7.35, for 10 min. The cells were washed twice with plating medium and plated on multiwell-plates (1.5×10$^5$ cells per ml) using the following defined medium: F-12/DMEM/BGJ(6:3:1) (Gibco: 430–1700/430–1600/320–2591) with 2 g BSA/L., 2.38 g Hepes/L.,50 mg Gentamycin/L (Schering Co.). The medium in each well was supplemented either with the novel peptide or natural GRF(1–44)-$NH_2$ (SEQ ID NO: 1-$NH_2$) at concentrations ranging from 3.1 to 200 fmol. per ml. of medium. Control wells contained no supplement. Plating was done with this medium added with 2% fetal calf serum to ensure rapid fixation of the cells. On the fourth day the cells were washed twice with the defined medium without fetal calf serum. Finally 900 ml of defined medium was added to each well plus 100 ml of the same medium containing each individual treatment, in triplicate. After 3 hours of incubation the medium was collected and diluted as required to conduct radioimmunoassay (RIA) for rat growth hormone. RIAs were conducted using Sinha's anti-murine GH immune serum and procedures according to the National Pituitary Agency using protein A to precipitate antibody antigen complex. The results are summarized in Table 1.

TABLE 1

| Potency of GRF Analogs Relative to GRF(1–44)-$NH_2$ (SEQ ID NO: 1-$NH_2$) | |
| --- | --- |
| SEQ ID NO: 1-$NH_2$ | 1.00 |
| SEQ ID NO: 34-$NH_2$ where $Xaa^1$ is desNH$_2$Tyr and $Xaa^2$ is D-Ala | 4.71 |
| SEQ ID NO: 9-$NH_2$ | 3.55 |
| SEQ ID NO: 8-$NH_2$ | 3.77 |
| SEQ ID NO: 10-$NH_2$ | 4.57 |
| SEQ ID NO: 13-OH | 2.79 |
| SEQ ID NO: 14-OH | 3.11 |
| SEQ ID NO: 17-OH, where $Xaa^2$ is D-Ala | 3.23 |
| SEQ ID NO: 23-OH | 2.96 |
| SEQ ID NO: 31-OH, where $Xaa^1$ is desNH$_2$Tyr and $Xaa^2$ is D-Ala | 4.20 |

EXAMPLE 20

In Vivo GRF Analog Administration

In vivo GRF analog studies were performed in crossbred swine (approximately 70 lbs; Hoffmann-La Roche Experimental Research Facility) housed in individual metabolism cages with food and water freely available. For each GRF analog examined, six pigs were arranged in a 6×6 latin square design, such that each pig received a different dose (0 [saline], 0.3, 1.0, 3.0, 6.0 or 10.0 μg/kg body weight) over a six day period. No "carry-over" effect of previous day's GRF analog dosing on subsequent GH responses was observed with any animal examined (ca. 16 hr "washout" period). All swine were cannulated via the femoral artery under halothane/ketamine HCL/xylezine anesthesia for subsequent (2–3 days) blood sampling. GRF analog was administered by subcutaneous injection in porcine gelatin. Pre-treatment (control) blood samples were taken every 30 min from 8:30–9:30 a.m. Treatment doses were administered beginning at 10:00 a.m. One hr post-dosing, animals were sampled at 10 min intervals; 2nd hr post-dosing, animals were sampled at 15 min intervals; 3rd hr post-dosing, animals were sampled at 30 min intervals. All samples were centrifuged and the serum fractions stored (−20° C.) until assayed for GH.

GH levels in porcine sera were measured by homologous double-antibody RIA, employing porcine GH standard (lot# AFP-10859C) supplied by Dr. A. Parlow (Research and Education Institute, Torrance, Calif.) and baboon anti-pGH sera (B-58: Hoffmann-La Roche). The pGH antisera employed in these assays did not cross-react (<1600 ng/ml) with porcine FSH (follicle stimulating hormone), porcine ACTH (adrenocorticotrophic hormone), porcine PRL (prolactin), or human GH. The least detectable GH concentration was 1.56 ng/ml (0.156 ng/100 ml sample), with 50% displacement observed at 12.13 ng/ml. Serial dilutions of spiked (with pGH) or non-spiked serum exhibited parallelism with the pGH standard curve. Inter-assay and intra-assay coefficients of variation were 9.6 and 6.2%, respectively. GH area under the curve (GH AUC) for the treatment period (0–360 min) was determined by trapezoidal summation. Mean GH AUC and mean GH peak data were independently compared using a one-way analysis of variance (repeated measures ANOVA) and Fisher least significant difference ($LSD_{.05}$).

The results of the assays were that SEQ ID NO: 13-OH and SEQ ID NO: 14-OH, two of the novel compounds of the instant invention, and SEQ ID NO: 35-OH, were similarly potent to SEQ ID NO: 34-$NH_2$ where $Xaa^1$ is des$NH_2$Tyr and $Xaa^2$ is D-Ala (disclosed in U.S. Pat. 4,649,131) as estimated by GH AUC (Dose range: 0.0, 0.3, 1.0, 3.0, and 6.0 mg/kg). SEQ ID NO: 34-$NH_2$ where $Xaa^1$ is des$NH_2$Tyr and $Xaa^2$ is D-Ala is 10–15 times more potent than GRF (1–29)-$NH_2$ (SEQ ID NO: 3-$NH_2$).

EXAMPLE 21

Half-life stability of GRF analogs in aqueous solution was determined by reverse phase HPLC at 37° C. GRF analogs were prepared as described above. GRF analogs were dissolved in 20 mL of $H_2O$ and then taken up in 1.0 mL of buffer solution (pH 7.40) containing 0.25M $Na_2HPO_4$/$H_3PO_4$ and 1.0 mM $NaN_3$. The concentration of the GRF analogs was 0.15 mg/mL. The HPLC system was a Laboratory Data Control (LDC) HPLC with a Waters C-18 column (3.9×300 mm, 10µ). The detector was a LDC Spectromonitor III and the gradient delivery system was a Constametric II. Mobile phase—(A) 0.025% TFA in $H_2O$, (B) 0.025% TFA in acetonitrile. Gradient was 0–37% (B) in 15 minutes for SEQ ID NO: 8-$NH_2$ where $Xaa^1$ is des$NH_2$Tyr and $Xaa^2$ is D-Ala and SEQ ID NO: 9-$NH_2$ where $Xaa^1$ is des$NH_2$Tyr and $Xaa^2$ is D-Ala; 0-35% (B) in 15 minutes for SEQ ID NO: 35-$NH_2$ where $Xaa^1$ is des$NH_2$Tyr and $Xaa^2$ is D-Ala; and 0–36% (B) in 15 minutes for SEQ ID NO: 10-$NH_2$ where $Xaa^1$ is des$NH_2$Tyr and $Xaa^2$ is D-Ala. Flow rate for all gradients was 2 ml/minute. Detection was at 206 nm using a UV detector. The results appear in the table below.

| HALF-LIFE STABILITY IN AQUEOUS SOLUTION AT 37° C. | |
| --- | --- |
| COMPOUND | HALF-LIFE $t_{(½)}$, hrs |
| SEQ ID NO: 35-$NH_2$ where $Xaa^1$ is des$NH_2$Tyr and $Xaa^2$ is D-Ala | 72 |
| SEQ ID NO: 10-$NH_2$ where $Xaa^1$ is des$NH_2$Tyr and $Xaa^2$ is D-Ala | 122 |
| SEQ ID NO: 8-$NH_2$ where $Xaa^1$ is des$NH_2$Tyr and $Xaa^2$ is D-Ala | 169 |
| SEQ ID NO: 9-$NH_2$ where $Xaa^1$ is des$NH_2$Tyr and $Xaa^2$ is D-Ala | 180 |

What is claimed is:

1. A compound having a sequence of from about twenty-nine (29) to about forty-four (44) amino acids (SEQ ID NO: 6) wherein Xaa at position 1 is desNH$_2$Tyr, His, desNH$_2$His, or 3-MeHis; Xaa at position 2 is Val, Leu, Ile, Ala, D-Ala, N-Methyl-D-Ala, Gly, Nle or Nval; Xaa at position 8 is Gln, Ser, or Thr; Xaa at position 15 is Ala; Xaa at position 27 is Met, Nle, or Leu; Xaa at position 28 is Ser or Asn; Xaa at position 29 is an amino acid sequence (SEQ ID NO: 7) or fragments thereof where the fragment is reduced in number from one to fifteen amino acid residues from the carboxyl-terminus, where the carboxyl-terminus can be the free carboxylic acid or the corresponding amide, and the pharmaceutically acceptable acid or based addition salts thereof.

2. The compound of claim 1, wherein Xaa at position 15 is Ala, Xaa at position 27 is Met, Xaa at position 28 is Ser and Xaa at position 29 is Arg.

3. The compound of claim 2, wherein Xaa at position 1 is desNH$_2$Tyr and Xaa at position 2 is D-Ala.

4. The compound of claim 3 selected from the group consisting of SEQ ID NO: 8-NH$_2$, SEQ ID NO: 9-NH$_2$, and SEQ ID NO: 10-NH$_2$.

5. The compound of claim 1, where Xaa at position 15 is Ala and Xaa at position 29 is Arg-Gln-Gln-Gly (residues 1–4 of SEQ ID NO:7).

6. The compound of claim 5, wherein Xaa at position 2 is Val or D-Ala.

7. The compound of claim 6, wherein Xaa at position 1 is selected from the group consisting of desNH$_2$Tyr and His.

8. The compound of claim 7, wherein Xaa at position 27 is Leu.

9. The compound of claim 8, wherein Xaa at position 1 is His.

10. The compound of claim 9 selected from the group consisting of SEQ ID NO: 11-OH, SEQ ID NO: 13-OH, and SEQ ID NO: 15-OH.

11. The compound of claim 8, wherein Xaa at position 1 is desNH$_2$Tyr.

12. The compound of claim 11, SEQ ID NO: 24-OH where Xaa at position 1 is desNH$_2$Tyr.

13. The compound of claim 8, SEQ ID NO: 31-OH where Xaa at position 1 is desNH$_2$Tyr and Xaa at position 2 is D-Ala.

14. The compound of claim 9, wherein Xaa at position 28 is Asn.

15. The compound of claim 14 selected from the group consisting of SEQ ID NO: 12-OH, SEQ. ID NO: 14-OH, and SEQ ID NO: 16-OH.

16. The compound of claim 5, wherein Xaa at position 2 is selected from the group consisting of Ala or D-Ala.

17. The compound of claim 16, SEQ ID NO:17-OH where Xaa at position 2 is D-Ala.

18. A pharmaceutical composition for stimulating the release of growth hormone in warm or cold-blooded animals comprising a compound having a sequence of from about twenty-nine (29) to about forty-four (44) amino acids (SEQ ID NO: 6) wherein Xaa at position 1 is Tyr, desNH$_2$Tyr, His, desNH$_2$His, or 3-MeHis; Xaa at position 2 is Val, Leu, Ile, Ala, D-Ala, N-Methyl-D-Ala, Gly, Nle or Nval; Xaa at position 8 is Gln, Ser, or Thr; Xaa at position 15 is Ala or Leu; Xaa at position 27 is Met, Nle, or Leu; Xaa at position 28 is Ser or Asn; Xaa at position 29 is an amino acid sequence (SEQ ID NO: 7) or fragments thereof where the fragment is reduced in number from one to fifteen amino acid residues from the carboxy-terminus, where the carboxyl-terminus can be the free carboxylic acid or the corresponding amide, and the pharmaceutically acceptable acid or base addition salts thereof, and a pharmaceutically acceptable carrier.

19. A method of treating growth hormone related disorders characterized by growth hormone deficiencies or for improvement of growth performance in warm or cold-blooded animals comprising administering to said animal in need of such treatment a compound having a sequence of from about twenty-nine (29) to about forty-four (44) amino acids (SEQ ID NO: 6) wherein Xaa at position 1 is Tyr, desNH$_2$Tyr, His, desNH$_2$His, or 3-MeHis; Xaa at position 2 is Val, Leu, Ile, Ala, D-Ala, N-Methyl-D-Ala, Gly, Nle or Nval; Xaa at position 8 is Gln, Ser, or Thr; Xaa at position 15 is Ala or Leu; Xaa at position 27 is Met, Nle, or Leu; Xaa at position 28 is Ser or Asn; Xaa at position 29 is an amino acid sequence (SEQ ID NO: 7) or fragments thereof where the fragment is reduced in number from one to fifteen amino acid residues from the carboxyl-terminus, where the carboxyl-terminus can be the free carboxylic acid or the corresponding amide, and the pharmaceutically acceptable acid or base addition salts thereof, which is effective in treating growth hormone related disorders characterized by growth hormone deficiencies or for improvement of growth performance in warm or cold-blooded animals.

* * * * *

UNITED STATES PATENT AND TRADEMARK OFFICE
CERTIFICATE OF CORRECTION

PATENT NO. : 5,846,936
DATED : December 8, 1998
INVENTOR(S) : FELIX ET AL.

It is certified that error appears in the above-identified patent and that said Letters Patent is hereby corrected as shown below:

In Column 36, line 21, (claim 18, line 5) delete "Tyr," first instance.

In Column 36, line 23, (claim 18, line 7) delete "Ala,".

In Column 36, line 39, (claim 19, line 7) delete "Tyr," last word.

In Column 36, line 41, (claim 19, line 9) delete "Ala," first Instance.

Signed and Sealed this

Twenty-fifth Day of May, 1999

Attest:

Q. TODD DICKINSON

*Attesting Officer*   *Acting Commissioner of Patents and Trademarks*

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
      (A) LENGTH: 44 amino acids
      (B) TYPE: amino acid
      (D) TOPOLOGY: linear (ii) MOLECULE TYPE: peptide (xi) SEQUENCE DESCRIPTION: SEQ ID NO:1:

```
Tyr  Ala  Asp  Ala  Ile  Phe  Thr  Asn  Ser  Tyr  Arg  Lys  Val  Leu  Gly  Gln
1                   5                        10                       15

Leu  Ser  Ala  Arg  Lys  Leu  Leu  Gln  Asp  Ile  Met  Ser  Arg  Gln  Gln  Gly
               20                       25                       30

Glu  Ser  Asn  Gln  Glu  Arg  Gly  Ala  Arg  Ala  Arg  Leu
               35                       40
```

(2) INFORMATION FOR SEQ ID NO:2:

(i) SEQUENCE CHARACTERISTICS:
      (A) LENGTH: 40 amino acids
      (B) TYPE: amino acid
      (D) TOPOLOGY: linear (ii) MOLECULE TYPE: peptide (xi) SEQUENCE DESCRIPTION: SEQ ID NO:2:

```
Tyr  Ala  Asp  Ala  Ile  Phe  Thr  Asn  Ser  Tyr  Arg  Lys  Val  Leu  Gly  Gln
1                   5                        10                       15

Leu  Ser  Ala  Arg  Lys  Leu  Leu  Gln  Asp  Ile  Met  Ser  Arg  Gln  Gln  Gly
```

```
                              20                      25                       30

Glu  Ser  Asn  Gln  Glu  Arg  Gly  Ala
                              35                      40
```

( 2 ) INFORMATION FOR SEQ ID NO:3:

( i ) SEQUENCE CHARACTERISTICS:
    ( A ) LENGTH: 29 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:3:

```
        Tyr  Ala  Asp  Ala  Ile  Phe  Thr  Asn  Ser  Tyr  Arg  Lys  Val  Leu  Gly  Gln
        1                   5                        10                       15

Leu  Ser  Ala  Arg  Lys  Leu  Leu  Gln  Asp  Ile  Met  Ser  Arg
                             20                      25
```

( 2 ) INFORMATION FOR SEQ ID NO:4:

( i ) SEQUENCE CHARACTERISTICS:
    ( A ) LENGTH: 32 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:4:

```
        Tyr  Ala  Asp  Ala  Ile  Phe  Thr  Asn  Ser  Tyr  Arg  Lys  Val  Leu  Gly  Gln
        1                   5                        10                       15

Leu  Ser  Ala  Arg  Lys  Leu  Leu  Gln  Asp  Ile  Leu  Ser  Arg  Gln  Gln  Gly
                             20                      25                       30
```

( 2 ) INFORMATION FOR SEQ ID NO:5:

( i ) SEQUENCE CHARACTERISTICS:
    ( A ) LENGTH: 32 amino acids
    ( B ) TYPE: amino acid
    ( D ) TOPOLOGY: linear ( i i ) MOLECULE TYPE: protein ( x i ) SEQUENCE DESCRIPTION: SEQ ID NO:5:

```
        Tyr  Ala  Asp  Ala  Ile  Phe  Thr  Xaa  Ser  Tyr  Arg  Lys  Val  Leu  Gly  Gln
        1                   5                        10                       15

Leu  Ser  Ala  Arg  Lys  Leu  Leu  Gln  Asp  Ile  Leu  Ser  Arg  Gln  Gln  Gly
                             20                      25                       30
```

( 2 ) INFORMATION FOR SEQ ID NO:6:

( i ) SEQUENCE CHARACTERISTICS:
    ( A ) LENGTH: 29 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:6:

```
        Xaa  Xaa  Asp  Ala  Ile  Phe  Thr  Xaa  Ser  Tyr  Arg  Lys  Val  Leu  Xaa  Gln
        1                   5                        10                       15

Leu  Ser  Ala  Arg  Lys  Leu  Leu  Gln  Asp  Ile  Xaa  Xaa  Xaa
                             20                      25
```

( 2 ) INFORMATION FOR SEQ ID NO:7:

( i ) SEQUENCE CHARACTERISTICS:
   ( A ) LENGTH: 16 amino acids
   ( B ) TYPE: amino acid
   ( D ) TOPOLOGY: linear ( i i ) MOLECULE TYPE: peptide ( x i ) SEQUENCE DESCRIPTION: SEQ ID NO:7:

Arg Gln Gln Gly Glu Ser Asn Gln Glu Arg Gly Ala Arg Ala Arg Leu
1               5                   10                  15

( 2 ) INFORMATION FOR SEQ ID NO:8:

( i ) SEQUENCE CHARACTERISTICS:
      ( A ) LENGTH: 29 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:8:

Xaa Xaa Asp Ala Ile Phe Thr Thr Ser Tyr Arg Lys Val Leu Ala Gln
1               5                   10                  15

Leu Ser Ala Arg Lys Leu Leu Gln Asp Ile Met Ser Arg
                20                  25

( 2 ) INFORMATION FOR SEQ ID NO:9:

( i ) SEQUENCE CHARACTERISTICS:
      ( A ) LENGTH: 29 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:9:

Xaa Xaa Asp Ala Ile Phe Thr Ser Ser Tyr Arg Lys Val Leu Ala Gln
1               5                   10                  15

Leu Ser Ala Arg Lys Leu Leu Gln Asp Ile Met Ser Arg
                20                  25

( 2 ) INFORMATION FOR SEQ ID NO:10:

( i ) SEQUENCE CHARACTERISTICS:
      ( A ) LENGTH: 29 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:10:

Xaa Xaa Asp Ala Ile Phe Thr Gln Ser Tyr Arg Lys Val Leu Ala Gln
1               5                   10                  15

Leu Ser Ala Arg Lys Leu Leu Gln Asp Ile Met Ser Arg
                20                  25

( 2 ) INFORMATION FOR SEQ ID NO:11:

( i ) SEQUENCE CHARACTERISTICS:
      ( A ) LENGTH: 32 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:11:

His Val Asp Ala Ile Phe Thr Thr Ser Tyr Arg Lys Val Leu Ala Gln
1               5                   10                  15

```
              Leu  Ser  Ala  Arg  Lys  Leu  Leu  Gln  Asp  Ile  Leu  Ser  Arg  Gln  Gln  Gly
                             20                  25                            30
```

(2) INFORMATION FOR SEQ ID NO:12:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:12:

```
              His  Val  Asp  Ala  Ile  Phe  Thr  Thr  Ser  Tyr  Arg  Lys  Val  Leu  Ala  Gln
              1                    5                        10                         15

Leu  Ser  Ala  Arg  Lys  Leu  Leu  Gln  Asp  Ile  Leu  Asn  Arg  Gln  Gln  Gly
                             20                  25                            30
```

(2) INFORMATION FOR SEQ ID NO:13:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:13:

```
              His  Val  Asp  Ala  Ile  Phe  Thr  Gln  Ser  Tyr  Arg  Lys  Val  Leu  Ala  Gln
              1                    5                        10                         15

Leu  Ser  Ala  Arg  Lys  Leu  Leu  Gln  Asp  Ile  Leu  Ser  Arg  Gln  Gln  Gly
                             20                  25                            30
```

(2) INFORMATION FOR SEQ ID NO:14:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:14:

```
              His  Val  Asp  Ala  Ile  Phe  Thr  Gln  Ser  Tyr  Arg  Lys  Val  Leu  Ala  Gln
              1                    5                        10                         15

Leu  Ser  Ala  Arg  Lys  Leu  Leu  Gln  Asp  Ile  Leu  Asn  Arg  Gln  Gln  Gly
                             20                  25                            30
```

(2) INFORMATION FOR SEQ ID NO:15:

(i) SEQUENCE CHARACTERISTICS:
        (A) LENGTH: 32 amino acids
        (B) TYPE: amino acid
        (D) TOPOLOGY: linear (ii) MOLECULE TYPE: peptide (xi) SEQUENCE DESCRIPTION: SEQ ID NO:15:

```
              His  Val  Asp  Ala  Ile  Phe  Thr  Ser  Ser  Tyr  Arg  Lys  Val  Leu  Ala  Gln
              1                    5                        10                         15

Leu  Ser  Ala  Arg  Lys  Leu  Leu  Gln  Asp  Ile  Leu  Ser  Arg  Gln  Gln  Gly
                             20                  25                            30
```

(2) INFORMATION FOR SEQ ID NO:16:

(i) SEQUENCE CHARACTERISTICS:

(A) LENGTH: 32 amino acids
(B) TYPE: amino acid
(D) TOPOLOGY: linear (ii) MOLECULE TYPE: peptide (xi) SEQUENCE DESCRIPTION: SEQ ID NO:16:

His Val Asp Ala Ile Phe Thr Ser Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

(2) INFORMATION FOR SEQ ID NO:17:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:17:

His Xaa Asp Ala Ile Phe Thr Gln Ser Tyr Arg Lys Val Leu Ala Gln
1               5                   10                  15

Leu Ser Ala Arg Lys Leu Leu Gln Asp Ile Leu Ser Arg Gln Gln Gly
            20                  25                  30

(2) INFORMATION FOR SEQ ID NO:18:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:18:

Tyr Val Asp Ala Ile Phe Thr Gln Ser Tyr Arg Lys Val Leu Ala Gln
1               5                   10                  15

Leu Ser Ala Arg Lys Leu Leu Gln Asp Ile Leu Asn Arg Gln Gln Gly
            20                  25                  30

(2) INFORMATION FOR SEQ ID NO:19:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:19:

Tyr Val Asp Ala Ile Phe Thr Gln Ser Tyr Arg Lys Val Leu Ala Gln
1               5                   10                  15

Leu Ser Ala Arg Lys Leu Leu Gln Asp Ile Leu Ser Arg Gln Gln Gly
            20                  25                  30

(2) INFORMATION FOR SEQ ID NO:20:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:20:

```
Tyr  Val  Asp  Ala  Ile  Phe  Thr  Thr  Ser  Tyr  Arg  Lys  Val  Leu  Ala  Gln
1                   5                        10                       15

Leu  Ser  Ala  Arg  Lys  Leu  Leu  Gln  Asp  Ile  Leu  Asn  Arg  Gln  Gln  Gly
               20                       25                       30
```

( 2 ) INFORMATION FOR SEQ ID NO:21:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

```
Tyr  Val  Asp  Ala  Ile  Phe  Thr  Ser  Ser  Tyr  Arg  Lys  Val  Leu  Ala  Gln
1                   5                        10                       15

Leu  Ser  Ala  Arg  Lys  Leu  Leu  Gln  Asp  Ile  Leu  Ser  Arg  Gln  Gln  Gly
               20                       25                       30
```

( 2 ) INFORMATION FOR SEQ ID NO:22:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Tyr  Val  Asp  Ala  Ile  Phe  Thr  Ser  Ser  Tyr  Arg  Lys  Val  Leu  Ala  Gln
1                   5                        10                       15

Leu  Ser  Ala  Arg  Lys  Leu  Leu  Gln  Asp  Ile  Leu  Asn  Arg  Gln  Gln  Gly
               20                       25                       30
```

( 2 ) INFORMATION FOR SEQ ID NO:23:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
His  Ala  Asp  Ala  Ile  Phe  Thr  Gln  Ser  Tyr  Arg  Lys  Val  Leu  Ala  Gln
1                   5                        10                       15

Leu  Ser  Ala  Arg  Lys  Leu  Leu  Gln  Asp  Ile  Leu  Ser  Arg  Gln  Gln  Gly
               20                       25                       30
```

( 2 ) INFORMATION FOR SEQ ID NO:24:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

```
Xaa  Val  Asp  Ala  Ile  Phe  Thr  Gln  Ser  Tyr  Arg  Lys  Val  Leu  Ala  Gln
1                   5                        10                       15

Leu  Ser  Ala  Arg  Lys  Leu  Leu  Gln  Asp  Ile  Leu  Ser  Arg  Gln  Gln  Gly
               20                       25                       30
```

( 2 ) INFORMATION FOR SEQ ID NO:25:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:25:

Leu Gln Asp Ile Leu Asn Arg Gln Gln Gly
1               5                   10

( 2 ) INFORMATION FOR SEQ ID NO:26:

( i ) SEQUENCE CHARACTERISTICS:
  ( A ) LENGTH: 24 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:26:

Ser Tyr Arg Lys Val Leu Ala Gln Leu Ser Ala Arg Lys Leu Leu Gln
1               5                   10                  15
Asp Ile Leu Asn Arg Gln Gln Gly
                20

( 2 ) INFORMATION FOR SEQ ID NO:27:

( i ) SEQUENCE CHARACTERISTICS:
  ( A ) LENGTH: 30 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:27:

Asp Ala Ile Phe Thr Thr Ser Tyr Arg Lys Val Leu Ala Gln Leu Ser
1               5                   10                  15
Ala Arg Lys Leu Leu Gln Asp Ile Leu Asn Arg Gln Gln Gly
                20                  25                  30

( 2 ) INFORMATION FOR SEQ ID NO:28:

( i ) SEQUENCE CHARACTERISTICS:
  ( A ) LENGTH: 30 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:28:

Asp Ala Ile Phe Thr Ser Ser Tyr Arg Lys Val Leu Ala Gln Leu Ser
1               5                   10                  15
Ala Arg Lys Leu Leu Gln Asp Ile Leu Asn Arg Gln Gln Gly
                20                  25                  30

( 2 ) INFORMATION FOR SEQ ID NO:29:

( i ) SEQUENCE CHARACTERISTICS:
  ( A ) LENGTH: 24 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:29:

Ser Tyr Arg Lys Val Leu Ala Gln Leu Ser Ala Arg Lys Leu Leu Gln

```
              1               5                   10                  15
        Asp Ile Leu Ser Arg Gln Gln Gly
                         20
```

( 2 ) INFORMATION FOR SEQ ID NO:30:

( i ) SEQUENCE CHARACTERISTICS:
      ( A ) LENGTH: 30 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:30:

```
        Asp Ala Ile Phe Thr Gln Ser Tyr Arg Lys Val Leu Ala Gln Leu Ser
        1               5                   10                  15
        Ala Arg Lys Leu Leu Gln Asp Ile Leu Ser Arg Gln Gln Gly
                        20                  25                  30
```

( 2 ) INFORMATION FOR SEQ ID NO:31:

( i ) SEQUENCE CHARACTERISTICS:
      ( A ) LENGTH: 32 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:31:

```
        Xaa Xaa Asp Ala Ile Phe Thr Gln Ser Tyr Arg Lys Val Leu Ala Gln
        1               5                   10                  15
        Leu Ser Ala Arg Lys Leu Leu Gln Asp Ile Leu Ser Arg Gln Gln Gly
                        20                  25                  30
```

( 2 ) INFORMATION FOR SEQ ID NO:32:

( i ) SEQUENCE CHARACTERISTICS:
      ( A ) LENGTH: 30 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:32:

```
        Asp Ala Ile Phe Thr Thr Ser Tyr Arg Lys Val Leu Ala Gln Leu Ser
        1               5                   10                  15
        Ala Arg Lys Leu Leu Gln Asp Ile Leu Ser Arg Gln Gln Gly
                        20                  25                  30
```

( 2 ) INFORMATION FOR SEQ ID NO:33:

( i ) SEQUENCE CHARACTERISTICS:
      ( A ) LENGTH: 21 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:33:

```
        Ser Tyr Arg Lys Val Leu Ala Gln Leu Ser Ala Arg Lys Leu Leu Gln
        1               5                   10                  15
        Asp Ile Met Ser Arg
                        20
```

( 2 ) INFORMATION FOR SEQ ID NO:34:

( i ) SEQUENCE CHARACTERISTICS:
  ( A ) LENGTH: 29 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:34:

```
Xaa Xaa Asp Ala Ile Phe Thr Asn Ser Tyr Arg Lys Val Leu Ala Gln
1               5                   10                  15

Leu Ser Ala Arg Lys Leu Leu Gln Asp Ile Met Ser Arg
            20                  25
```

( 2 ) INFORMATION FOR SEQ ID NO:35:

( i ) SEQUENCE CHARACTERISTICS:
    ( A ) LENGTH: 32 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:35:

```
His Val Asp Ala Ile Phe Thr Asn Ser Tyr Arg Lys Val Leu Ala Gln
1               5                   10                  15

Leu Ser Ala Arg Lys Leu Leu Gln Asp Ile Leu Ser Arg Gln Gln Gly
            20                  25                  30
```

( 2 ) INFORMATION FOR SEQ ID NO:36:

( i ) SEQUENCE CHARACTERISTICS:
    ( A ) LENGTH: 32 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:36:

```
Tyr Val Asp Ala Ile Phe Thr Thr Ser Tyr Arg Lys Val Leu Ala Gln
1               5                   10                  15

Leu Ser Ala Arg Lys Leu Leu Gln Asp Ile Leu Ser Arg Gln Gln Gly
            20                  25                  30
```

( 2 ) INFORMATION FOR SEQ ID NO:37:

( i ) SEQUENCE CHARACTERISTICS:
    ( A ) LENGTH: 32 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:37:

```
His Val Asp Ala Ile Phe Thr Gln Ser Tyr Arg Lys Val Leu Leu Gln
1               5                   10                  15

Leu Ser Ala Arg Lys Leu Leu Gln Asp Ile Leu Ser Arg Gln Gln Gly
            20                  25                  30
```

( 2 ) INFORMATION FOR SEQ ID NO:38:

( i ) SEQUENCE CHARACTERISTICS:
    ( A ) LENGTH: 32 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:38:

-continued

| His | Val | Asp | Ala | Ile | Phe | Thr | Ser | Ser | Arg | Lys | Val | Leu | Ala | Gln |
|-----|-----|-----|-----|-----|-----|-----|-----|-----|-----|-----|-----|-----|-----|-----|
| 1   |     |     |     | 5   |     |     |     |     | Tyr |     |     |     |     |     |
|     |     |     |     |     |     |     |     | 10  |     |     |     |     | 15  |     |
| Leu | Ser | Ala | Arg | Lys | Leu | Leu | Gln | Asp | Ile | Xaa | Ser | Arg | Gln | Gln | Gly |
|     |     |     | 20  |     |     |     |     | 25  |     |     |     | 30  |     |     |     |